United States Patent [19]
Fuchs

[11] Patent Number: 5,486,322
[45] Date of Patent: Jan. 23, 1996

[54] PRODUCTION OF MULTILAYER PRODUCTIVE COVERINGS ON CONVENTIONAL DIP MOLDING LINES

[75] Inventor: Ingbert E. Fuchs, Desoto, Tex.

[73] Assignee: Board of Regents, The University of Texas System, Austin, Tex.

[21] Appl. No.: 129,111

[22] PCT Filed: Nov. 27, 1991

[86] PCT No.: PCT/US91/08954

§ 371 Date: Oct. 1, 1993

§ 102(e) Date: Oct. 1, 1993

[87] PCT Pub. No.: WO92/17124

PCT Pub. Date: Oct. 15, 1992

Related U.S. Application Data

[63] Continuation-in-part of Ser. No. 678,838, Apr. 1, 1991, which is a continuation-in-part of Ser. No. 422,913, Oct. 17, 1989, abandoned, which is a continuation-in-part of Ser. No. 359,474, May 22, 1989, abandoned.

[51] Int. Cl.⁶ .......................... B29C 41/14; B29C 44/06
[52] U.S. Cl. .......................... 264/46.5; 264/54; 264/300; 264/301; 264/305; 264/307; 264/308
[58] Field of Search .......................... 264/46.5, 54, 301, 264/305, 307, 308, 300; 156/79; 2/159, 161.6, 161.7, 167, 169

[56] References Cited

U.S. PATENT DOCUMENTS

| | | | |
|---|---|---|---|
| 3,136,832 | 6/1964 | Ballmer | 264/306 |
| 3,633,216 | 1/1972 | Schonholtz | 2/168 |
| 4,497,072 | 2/1985 | Watanabe | 2/169 |
| 4,500,358 | 2/1985 | Mayer et al. | 264/305 |
| 4,575,476 | 3/1986 | Podell et al. | 2/167 |
| 4,578,826 | 4/1986 | Adiletta | 2/167 |
| 4,901,372 | 2/1990 | Pierce | 2/167 |
| 4,919,966 | 4/1990 | Shlenker | 2/167.7 |
| 4,930,522 | 6/1990 | Busnel et al. | 128/844 |
| 4,935,260 | 6/1990 | Shlenker | 2/159 |
| 5,130,159 | 7/1992 | Shlenker et al. | 2/167 |
| 5,138,719 | 8/1992 | Orlianges et al. | 645/305 |
| 5,338,565 | 8/1994 | Shlenker et al. | 2/167 |

FOREIGN PATENT DOCUMENTS

| | | | |
|---|---|---|---|
| 579157 | 5/1956 | Canada | 264/307 |
| 0128531 | 12/1984 | European Pat. Off. . | |
| 59-54526 | 9/1982 | Japan . | |
| 752171 | 7/1956 | United Kingdom | 264/307 |

*Primary Examiner*—Allan R. Kuhns
*Attorney, Agent, or Firm*—Arnold, White & Durkee

[57] ABSTRACT

Method of making a multilayer protective covering such as a surgical glove, finger cot or condom. Mold with a first layer is dipped into a gas-releasing solution which comprises a release agent, a blowing agent, and/or a coagulant. The mold is then dipped into a layer-forming solution to form a second layer. Heat is applied and gas forms between the layers, separating the layers. An antimicrobial solution may replace gas between the layers.

48 Claims, 4 Drawing Sheets

PRODUCTION OF MULTILAYER PRODUCTIVE COVERINGS ON CONVENTIONAL DIP MOLDING LINES

This is a continuation-in-part of copending application Ser. No. 678,838, filed Apr. 1, 1991, which is a continuation-in-part of Ser. No. 422,913, filed on Oct. 17, 1989 (now abandoned), which is a continuation-in-part of Ser. No. 359,474, filed on May 2, 1989 (now abandoned).

This invention relates to protective coverings (e.g., gloves and condoms) for human body members, and methods for making such protective coverings. More particularly, this invention relates to coverings such as protective gloves which may be used for various purposes, including, for example, surgery or other medical procedures, or protection from hazardous chemical substances.

The design of protective gloves represents a struggle of competing interests. To increase the protective nature of the glove intuitively requires increasing the thickness of the glove material. However, by increasing the thickness of the glove material, the sense of feel for the wearer of the gloves is increasingly hampered. Thus, the glove designer must find a suitable compromise between safety and sense of feel.

This problem is particularly acute in the area of surgical gloves. The sense of feel in the hands of a surgeon is important for the proper handling of delicate instruments and the proper execution of precise surgical procedures. However, it is also desirable that the surgeon be protected from biohazardous agents which the surgeon may be exposed to from the patient. For example, the surgical patient may carry viruses such as HIV (Human Immunodeficiency Virus) or hepatitis. During surgery, the surgeon's gloves are frequently cut or punctured, exposing the surgeon to infection.

Also, it is desirable to protect the patient from germs on the surgeon's or technician's hands. Although medical personnel, of course, typically scrub their hands before performing surgical procedures, some germs may remain and be exposed to the patient upon puncturing or tearing the surgical gloves.

Surgical gloves known to the Applicant are generally made of latex, vinyl, or neoprene, i.e. thin elastic materials which provide reasonable tear resistance and allow for satisfactory sense of feel. However, the gloves may be easily torn or punctured with sharp surgical instruments. Furthermore, it is difficult for the surgeon to detect a small tear or puncture in the glove material during surgery since such a puncture is difficult to see, especially if the gloves are covered with a patient's body fluids. Thus, the surgeon has little warning of exposure.

In the chemical or hazardous material preparation and handling area, disadvantages in present gloves also exist. Although the sense of feel for these areas may not be as important as that for the surgeon, there is also often a risk or danger even with thicker protective gloves. The glove material may be degraded or penetrated after a period of time by various chemicals which the chemist handles.

Protective coverings for other parts of the body also exist. For example, finger cots (i.e. glove-like coverings which cover only one finger) are used in medical procedures, particularly in rectal and vaginal examinations. Condoms are used to cover the male reproductive organ during intercourse. In addition to the obvious purpose of a condom to trap semen and thereby minimize the possibility of pregnancy resulting from intercourse, condoms are also used to protect the partners from infections by sexually transmitted diseases. This has become increasingly important over recent years in preventing the spread of HIV.

In these and other protective coverings, similar problems and concerns exist, i.e. danger of tearing or ripping the covering balanced against the desire for sensitivity.

Thus it is a general object of this invention to provide protective coverings which address the disadvantages experienced by the above-described coverings.

In one broad aspect, the present invention provides a protective covering for a human body member, the protective covering having an inner and outer layer. A layer of protective solution (such as an antimicrobial solution) is disposed between the inner and outer layers, and an impermeable seal is provided between the layers to contain the protective solution therebetween. The solution layer is preferably less than about 0.12 millimeter (mm) average thickness, such that capillary forces are exerted on the two covering layers, thereby providing a mechanical-like coupling between the two covering layers.

The term "protective covering" is used to mean any covering used to protectively cover a human body member. The term "human body member" is used broadly to include all limbs and external protrusions of the human body, e.g., fingers, hands, arms, toes, feet, legs, head, penis, etc. In many situations, a human body member may be exposed to biohazardous substances such as infected body fluids, or hazardous chemicals. Coverings are often used to protect body members from exposure to hazardous substances. Thus, the term "protective covering" includes such items as gloves, finger cots, condoms, and the like.

In a preferred embodiment, the present invention provides a surgical glove having an inner and outer layer. A layer of antimicrobial solution is disposed between the inner and outer layers, and an impermeable seal between the layers is provided. As stated above, the solution layer is less than 0.12 mm in average thickness to provide a mechanical-like capillary coupling between the glove layers.

To maximize the capillary force exerted by the liquid layer, the average thickness of such layer is preferably between about 0.01 and 0.09 mm, most preferably between about 0.025 and 0.05 mm. Further, the liquid layer is preferably of substantially uniform thickness.

The term "antimicrobial solution" means herein a solution, typically aqueous, capable of killing or inactivating infectious agents, such as bacteria or virus. Thus, the term includes, for example, virucides, bactericides, antiseptic solutions, antiviral solutions, antibacterial solutions, etc. The term also includes spermicidal solutions, particularly applicable when the protective garment provided by the invention is a condom. The spermicidal solution used is preferably additionally virucidal and/or bactericidal.

The term "impermeable seal" is used to mean a seal which is substantially both fluid-tight and air-tight. The seal should be fluid-tight to prevent leakage of the protective solution between the layers, and should be air-tight to facilitate mechanical coupling between the two layers resulting from capillary forces exerted by the protective solution.

Typical virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

The glove of this invention can provide improved protection over single layer surgical gloves. If the layers of the glove are punctured or torn during surgery, the antimicrobial solution releases and attacks infectious agents before reaching the surgeon's hands, thus protecting the surgeon during operating procedures. Furthermore, when the glove becomes punctured during use, it may act to protect the patient from exposure to germs which may exist on the surgeon's hands. Tearing or puncturing the glove may provide quick and thorough release of the antimicrobial solution disposed between the layers.

Applicant has found that sense of feel is not significantly diminished by the double layers. By providing a solution layer of thickness in the ranges described above, capillary forces exerted by the liquid solution provide a mechanical-like coupling between the glove layers, so that the sense of feel for the wearer of the gloves is not significantly diminished.

In a preferred embodiment, the antimicrobial solution comprises a virucidal solution, such as aqueous nonoxynol-9. This substance is an effective virucide against such viruses as HIV and hepatitis, and thus provides a glove being particularly useful for performing medical procedures on infected patients. Preferably, the aqueous nonoxynol-9 has a concentration of between about 0.05% and 5% (volume/volume). Most preferably, the concentration is between about 0.25% and 1% (volume/volume). It is known that a concentration in this range is effective for killing viruses. Higher concentrations can also be used but may be irritable if contacted with the eyes.

In another embodiment, the antimicrobial solution comprises a bactericidal solution. Of course, the antimicrobial solution could include both virucidal and bactericidal agents.

In a preferred embodiment of a surgical glove provided by the present invention, the antimicrobial solution includes a dye. This embodiment provides an effective means for showing the surgeon the precise location of a tear or puncture in the glove. Thus, if the outer layer of the glove is punctured, the dye will seep out of the puncture hole and stain the area around the hole. If the inner layer is also punctured, the dye will seep through the inner hole and stain the surgeon's hand at the location of the puncture. This provides the surgeon the precise location of exposure so that the surgeon can decontaminate the area of puncture.

Many suitable dyes are available for use with this invention. A dye should preferably be selected which is FDA approved for internal and external use so as not to harm the patient or surgeon. Preferably, the dye is selected so that its color is easily detectable in a blood environment. Suitable dyes incudes FDA approved FD&C colors, for example, FD&C Blue #1 (MERCK Index #1350), FD&C Blue #2 (MERCK Index #4835), and FD&C Green #3 (MERCK Index #3876). These three dyes are particularly preferred since they have FDA approval for use in food, drugs, and cosmetics, and provide good indications of puncture in use with the present invention due to their intense colors (in relatively low concentrations). Preferably, the concentration of the dye in the antimicrobial solution is between about 0.3 to 0.5 grams/liter, providing a good compromise between economics and tear indication.

Many dyes are also bactericidal and thus provide the further function of attacking infectious agents. Another advantage provided by use of such dyes is that they can not generally be washed off with water. Thus, if the glove is punctured and the user's hand is stained by the dye, he must use alcohol to remove the stain, alcohol also being a bactericide. Thus, the area of the puncture is decontaminated while the dye stain is washed off.

Preferably, the volume of the antimicrobial solution disposed between the layers of an average-sized glove (e.g. size 7.5–8.5) is between about 2 and 3 milliliters. For a size 8.5 glove (surface area approximately 650 cm$^2$), this volume of liquid provides a solution layer thickness of around 0.03 to 0.05 mm, thereby providing good capillary coupling between the glove layers.

In a preferred embodiment, the inner and outer layers are made of latex. Alternatively, the layers may comprise vinyl or neoprene. Latex provides adequate tear resistance for surgical procedures and allows for a good sense of feel for the wearer.

In a preferred embodiment, the inner layer may include a rough outer surface. Alternatively, the outer layer may include a rough inner surface. This may provide the advantage of preventing the antimicrobial solution from being completely squeezed away from any glove areas which are compressed during normal usage.

For applications when one may be exposed to harmful chemicals, such as during handling or preparation of chemicals or other hazardous substances, another embodiment of the present invention provides a protective glove. The protective glove includes an inner layer, an outer layer, an impermeable seal between the inner and outer layers, and a layer of neutralizing solution (thickness as described above) disposed between the inner and outer layers.

The neutralizing solution disposed between the inner and outer layers can be appropriately selected for the particular application for which the glove is to be used. Preferably, the neutralizing solution should be selected such that if the outer layer of the glove is punctured or permeated, the neutralizing solution will neutralize the chemicals to which the glove is exposed and thus protect the hands of the wearer of the glove.

For example, if a chemist is to be handling acids, the neutralizing solution selected should be a basic or buffering solution which could neutralize the acid upon puncture of the glove before reaching the chemist's hands. As another example, if a person were handling neurotoxins one might place appropriate enzymatic agents between the glove layers which could cleave the neurotoxins upon contact.

Since the sense of feel for a chemist is usually not as critical as that for a surgeon, a thicker layer and more protective material than latex is preferably selected for the protective glove. For example, the inner and outer layers may be made of neoprene, nitrile, or any other suitable materials which are resistant to the types of materials to be handled and which are resistant to tearing or puncture.

Since the appropriate neutralizing solution disposed between the layers may vary depending upon the chemicals or materials to be handled, the seal between the layers preferably includes a zip lock seal. In this manner, the user of the glove can temporarily open the seal, place the appropriate neutralizing solution between the glove layers, and reseal the glove.

Additionally, the material between the glove layers may included a pH or other indicator which would change colors after a passage of time to indicate that the neutralizing agent has been used up, such that the gloves may no longer be effective. Upon such indication, the user could replace the old gloves with a new pair.

In a preferred embodiment, the protective solution includes a dye to give a visible warning upon release if the glove is leaking or becomes punctured. That is, the dye upon release will stain the area of puncture.

Another embodiment of the present invention provides a surgical glove including a dye associated with the glove in such a manner as to produce a visible stain if the glove becomes punctured or torn at the location of such puncture or tear.

The invention also extends to a finger cot having an inner layer, an outer layer, an impermeable seal between the layers, and a layer of antimicrobial solution (thickness as described above) disposed between the layers. The finger cot is substantially similar to the surgical glove described above, except that the finger cot is configured and used to cover only a single finger as opposed to an entire hand. The preferred embodiments of materials discussed above in relation to surgical gloves also apply to finger cots. Thus, for example, the antimicrobial solution of the finger cot preferably includes a dye.

The invention further provides a condom having an inner and outer layer, an impermeable seal between the layers, and a layer of antimicrobial solution (thickness as described above) disposed between the inner and outer layers. Preferably, the antimicrobial solution comprises a spermicidal solution, such as nonoxynol-9. Nonoxynol-9 is particularly preferred since it also acts as a virucidal agent for protection against HIV and hepatitis.

One potential problem which can arise with the double (or multi) layer protective coverings provided by this invention is that the two layers may tend to slip on each other during use. This potential problem is most likely to arise when the covering is inserted into and removed from a tight passage, as will typically occur when using a glove, finger cot or condom. To reduce this problem, the layers of the covering may be sealed (e.g., by heat stamping or gluing) at a plurality of points, thereby physically adhering the two layers at those points. This will reduce the likelihood of slippage of the covering during use.

It should be appreciated that the protective ability of the covering may be reduced at the sealed points, since a puncture of the covering at that precise location might not cause the release of the protective solution disposed between the layers. This is not likely to present a significant concern in relation to condoms and finger cots, since sharp objects are not generally encountered when using those items. Nevertheless, the potentially reduced protection of the covering should be appreciated and considered when selecting the number and pattern of sealed points on the covering.

Another broad aspect of this invention provides methods for making protective gloves, e.g., surgical gloves. One such method comprises the steps of providing a first glove on a hand-shaped form, the first glove having a hand portion and a wrist portion; dipping the first glove into an antimicrobial solution; placing a second glove having a hand portion and a wrist portion on the hand-shaped form over the first glove, and sealing the wrist portions of said gloves together, such that the antimicrobial solution is contained as a layer between the first and second gloves, the solution layer having an average thickness of less than about 0.12 mm.

A second method provided by this invention comprises the steps of providing a first glove on a hand-shaped form, the first glove having a hand portion and a wrist portion; placing a second glove on the hand-shaped form over the first glove, the second glove having a hand portion and a wrist portion; placing an antimicrobial solution between the first and second gloves, and sealing the wrist portions of said gloves together, such that the antimicrobial solution is contained as a layer (thickness as described above) between the first and second gloves.

The term "hand-shaped form" is used herein broadly to mean any structure having the shape of a human hand, e.g., a conventional ceramic or metal former. The term also encompasses an actual human hand.

The initial step in each of the two above-described methods comprises providing a first glove on a hand-shaped form. This can be accomplished, for example, by obtaining a glove from a commercial or other available source and stretching the glove over a hand-shaped form. Alternatively, it can be accomplished singly or repeatedly by dipping a hand-shaped form into latex or other material to coat the form with a layer of the material, and drying and/or curing the layer to form the first glove on the form.

A third method for making a protective glove provided by this invention comprises the steps of providing a first glove having a hand portion and a wrist portion; exposing the exterior surface of the first glove to a vacuum to expand said glove; placing an antimicrobial solution on the interior surface of the first glove; inserting a second glove having a hand portion and a wrist portion into the expanded first glove; removing the vacuum from the exterior surface of the first glove; and sealing the wrist portions of the first and second gloves together to contain the antimicrobial solution as a layer (thickness as described above) between the first and second gloves.

The first and second gloves in all three methods described above may be, for example, conventional latex surgical gloves, or gloves made of some other material.

This invention provides a fourth method for making a protective glove comprising the steps of providing an enclosed bag or balloon (i.e., an enveloped sheet of material) having two opposing hand-shaped sections; puncturing one of the hand-shaped sections; applying a vacuum to the interior of the punctured hand-shaped section such that the opposing hand-shaped section is drawn into said punctured section; releasing the vacuum; injecting an antimicrobial solution between the two hand-shaped sections and sealing the puncture, such that the antimicrobial solution is contained as a layer (thickness as described above) between said sections. The enclosed bag of material may be produced in a negative form based on two negative hand-shaped spaces.

A fifth method of making a protective glove includes dipping a substantially hand-shaped form (e.g., a ceramic former) into a first layer-forming solution to form a first layer. The first layer is dipped into a gas-releasing solution that releases gas when heated. The first layer is then dipped into a second layer-forming solution to form a second layer. Heat is applied to either the first or the second layers (or both) such that gas is released from the gas-releasing solution to form a gas-filled layer separating the first and second layers. The gas may then be replaced with an antimicrobial solution. The first and second layers may be sealed together at the wrist. The gas-releasing solution may include a release agent such as polydimethylsiloxane, a coagulant such as calcium nitrate, and/or a blowing agent such as sodium hydrogen carbonate or ammonium carbonate.

The methods described above to make gloves may also be used to make condoms or finger cots by varying the shape of the forms used. Substantially the same materials and methods apply for condoms and finger cots.

A preferred embodiment of each of the above-described methods comprises an additional step of adhering the two hand portions or sections together at a plurality of points. This provides the advantage of restricting slippage of the two hand portions or sections during use of the glove.

The hand portions or sections may be adhered together in a variety of ways, e.g., by glue or double-sided adhesive tape.

In a preferred embodiment, the adhering step is accomplished by spot-vulcanizing the hand portions together at a plurality of points. In this embodiment, the first and second gloves (or the enclosed bag in the fourth method described above) may comprise unvulcanized (i.e., green strength) latex. After spot-vulcanizing the hand portions or sections together at the desired points, the entire glove assembly may then be vulcanized. Due to the high temperature involved in such vulcanization, the antimicrobial solution disposed within the glove assembly preferably comprises a degassed liquid, so that the liquid will not emit gas during the vulcanization step.

BRIEF DESCRIPTION OF THE DRAWINGS

This invention is now described by reference to the appended drawings which illustrate particular preferred embodiments of this invention.

DETAILED DESCRIPTION OF THE INVENTION

Figure 1:
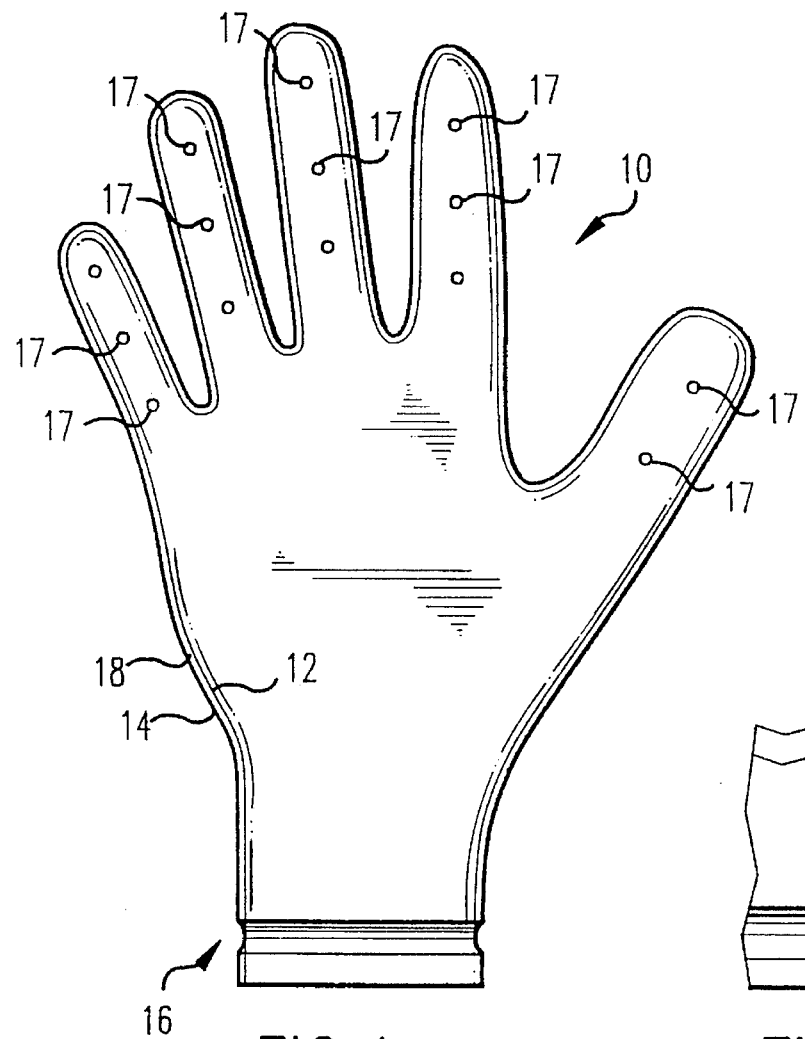
FIG. 1 is a side view of a glove prepared according to the present invention.

Referring now to FIG. 1, a preferred embodiment of the present invention is shown. A double layer glove 10 is illustrated having an inner layer 12, an outer layer 14, an impermeable seal 16 between the inner layer 12 and the outer layer 14, and a protective solution 18 disposed between the inner layer 12 and the outer layer 14. The solution layer 18 has an average thickness of less than about 0.12 mm, preferably between about 0.01 and 0.09 mm, even more preferably between about 0.025 and 0.05 mm, thereby maximizing the capillary coupling force between glove layers 12 and 14.

This glove is suitable for a broad range of applications, depending upon the selection of material for the inner and outer layers 12 and 14 and the protective solution 18. For use as a surgical glove, the inner and outer layers 12 and 14 are preferably made of latex. For such a surgical glove 10, protective solution 18 preferably comprises an antimicrobial solution. The antimicrobial solution preferably comprises a virucidal agent such as nonoxynol-9. The antimicrobial solution may also or alternatively include a bactericidal solution.

In a preferred embodiment, the antimicrobial solution 18 includes a dye. The dye will stain the area surrounding a puncture or tear in the glove, giving the surgeon a visual means for detecting areas of exposure.

In a preferred embodiment of the invention, the antimicrobial solution comprises nonoxynol-9 having a concentration of between about 0.05%–5% (v/v), most preferably about 0.5% (v/v), and a dye comprising FD&C Blue #1 having a concentration of between about 0.3 and 0.5 g/l.

In one preferred embodiment, the inner layer 12 includes a rough outer surface (i.e., the surface exposed to the antimicrobial solution 18). Single layer latex gloves are commercially available, wherein one may specify the roughness or coarseness of the surfaces of the glove.

In a preferred embodiment, the layers 12 and 14 are sealed (i.e., adhered) together at a plurality of points to reduce the likelihood that the layers slip on each other during use. As shown in FIG. 1, the fingers of the glove 10 may include a plurality of points 17 where the layers 12 and 14 have been adhered together. This feature is particularly advantageous when the fingers are used to explore or examine tight places. As illustrated in FIG. 1, the adhered points 17 are preferably located at the dorsal midpoint of the distal, middle, and proximal phalanges of each finger. By locating the points at the dorsal portion of the glove 10, sensitivity is not substantially impaired, but disassembly of the layers is restricted.

The adhered points may be formed by heating and pressing the inner and outer layers together at the desired places for a sufficient length of time for a seal to form. Alternatively, the layers may simply be glued together, or stuck together with double-sided adhesive tape, available commercially from, e.g., the 3M Company.

Figure 1A:
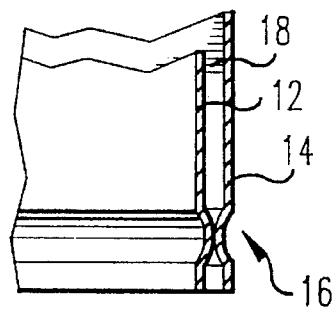
FIG. 1A is an enlarged, fragmentary, sectional side view illustrating the impermeable seal between the inner and outer layers of the glove of FIG. 1.
Figure 2:
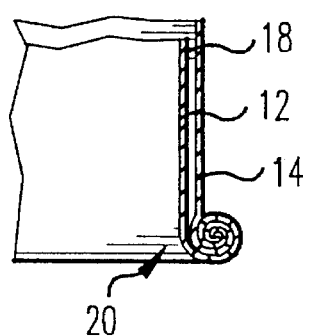
FIG. 2 is a fragmentary, sectional side view illustrating an alternate impermeable seal between the inner and outer layers of a glove in accordance with the present invention.
Figure 3:
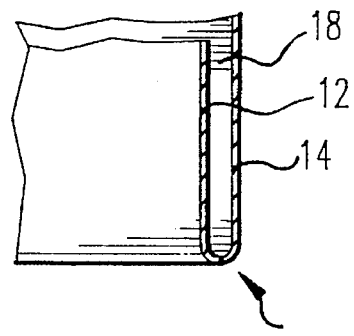
FIG. 3 is also a fragmentary, sectional side view showing another alternative of an impermeable seal.

The impermeable seal between the inner and outer layers 12 and 14 may take a variety of forms as illustrated in FIGS. 1A, 2 and 3. In FIG. 1A, the inner and outer layers 12 and 14 proximate the wrist area of the glove have been vulcanized or heat stamped to provide an impermeable seal 16. The seal 16 can be formed by simply applying heat and pressing the inner and outer layers 12 and 14 together around the circumference of the wrist area for a sufficient length of time for a seal to form.

Alternatively, inner layer 12 and outer layer 14 may be glued together to form an impermeable seal 20 as shown in FIG. 2. For example, with respect to a latex surgical glove, a latex glue can be conveniently used. Such glues are commercially available, e.g., 2141 Rubber Adhesive from the 3M Company. Alternatively, commercially available rubber cements can be used to create the seal between the layers. As a further alternative, shown in FIG. 3, inner layer 12 and outer layer 14 may be formed of a continuous sheet of material such that an impermeable seal 22 is provided by the roll connecting the inner and outer layers 12 and 14. Other fluid-tight seals may be used, for example, tape adhesive on both sides or a zip lock seal.

For chemical handling or preparation applications, the inner and outer layers 12 and 14 shown in FIG. 1 preferably comprise either neoprene or nitrile. A neutralizing solution 18 is disposed between the inner and outer layers 12 and 14. Furthermore, the seal 16 is preferably a zip lock type seal, so that the user can select and place an appropriate neutralizing solution between the layers depending upon the particular chemicals to be handled.

Several methods of preparing gloves provided by the present invention will now be described. These preparations will be discussed in the context of surgical gloves, although it should be understood that analogous preparations may be performed for other types of gloves and protective coverings.

In one preferred method, one places a first glove on his hand (or hand-shaped form). This first glove will eventually form the inner layer of a double-layer glove. The preparer of the glove dips his gloved hand into an antimicrobial solution and removes his hand from the solution. The preparer then places a second glove on his hand over the first glove. The second glove thus forms the outer layer of the double-layer glove. To form an impermeable seal between the first and second gloves, the preparer may peel a portion of the second glove away from his wrist. The preparer then applies glue or double adhesive tape to the outer surface of the first glove around the periphery proximate the wrist of the glove. The preparer then peels the wrist area of the second glove back over the first glove to form a glue seal.

In another preferred method, one places a first glove on a hand-shaped form. Next, glue or double-sided adhesive tape is placed at various points on the exterior of the first glove. Next, a second glove is placed over the first glove, whereby the glue or double-sided adhesive tape adheres the two gloves together at a plurality of points. Next, an antimicrobial solution is placed between the first and second gloves, e.g., by injecting the solution therebetween. Finally, the wrist portions of the two gloves are sealed (e.g., with glue or double-sided adhesive tape) to contain the antimicrobial solution between the two gloves.

In another preferred method, one dips a hand-shaped form (e.g., a ceramic former) in latex to form a layer of latex on the form. When the layer is sufficiently dry, a first "green" glove is thereby provided on the hand-shaped form. A second green strength (i.e., unvulcanized) latex glove is placed over the first glove, and a degassed antimicrobial liquid is disposed between the two gloves. (This may be accomplished either by dipping the first glove in the degassed antimicrobial liquid prior to applying the second glove, or injecting the degassed antimicrobial liquid between the two gloves after applying the second glove). Next, the wrist portions of the two gloves are adhered together by vulcanization to form an impermeable seal, thereby containing the antimicrobial solution between the two gloves. The two gloves may be adhered together at a plurality of points-by spot-vulcanizing them together at desired spots. Finally, the entire glove assembly is vulcanized.

Another suitable method of preparing a double-layer glove includes providing a first glove and exposing the exterior of the first glove to a vacuum environment. This first glove will eventually form the outer layer of the double-layer glove provided by the present invention. For example, the first glove may be inserted into a box through a box opening, wherein the wrist area of the first glove is temporarily sealed over the opening of the box in an air-tight arrangement. A vacuum is then applied to the interior of the box. This operates to expand the first glove like a balloon.

Next, a selected amount of antimicrobial solution is placed into the interior of the first glove. A second glove, which will form the inner layer of the double-layer glove, is now inserted into the expanded first glove. Preferably, the second glove is provided on a production form in the shape of a hand so that the second glove may be conveniently inserted in proper finger alignment with the first glove. The vacuum is then released and the first glove is released from the box opening. The first and second layers are then sealed proximate the wrist area.

A double-layer glove may be formed from a single piece of material, and thus provide a glove having a rolled seal as illustrated in FIG. 3. To make such a glove, a sheet of latex is first formed having two opposing glove-shaped sections. Such a sheet may be made using a negative form. Thus, one half of the sheet is in the shape of a hand, and the other half of the sheet is in the shape of an opposing hand. A puncture is made in one of the opposing hand sections and a vacuum is applied to the interior portion of that hand section. Due to the vacuum, the opposing hand section will be drawn into the first hand to provide a double layer glove. The hand section in which the puncture was made and vacuum applied forms the outer layer, and the opposing hand section forms the inner layer. The vacuum is then released and a selected amount of antimicrobial solution is injected between the two hand sections through the puncture opening in the outer glove section. The puncture opening is then sealed.

In another preferred method, a multilayer glove may be made by dipping a substantially hand-shaped form (e.g., a ceramic former) into a first layer-forming solution to form a first layer. The first layer may be dipped into a gas-releasing solution that releases gas when heated. The first layer may then be dipped into a second layer-forming solution to form a second layer. Heat may be applied to either the first or the second layers (or both) such that gas is released from the gas-releasing solution to form a gas-filled layer separating the first and second layers. The gas may then be replaced with an antimicrobial solution. The first and second layers may be sealed together at the wrist.

"Multilayer" as used herein means more than one layer in the finished protective covering. For instance, a preferred glove may include an inner layer, a middle layer filled with antimicrobial solution, and an outer layer. A covering may include only an inner layer and an outer layer, thus producing a two layer covering. Such a covering in the form of a glove may be preferred by some doctors who currently wear two gloves to prevent infection. Alternatively, the glove may comprise a plurality of layers, with each layer including different materials.

The hand-shaped form may be dipped more than once to form the first and subsequent layers. For instance, the form may be dipped twice or more in succession in the same layer-forming solution to form a layer.

The first layer is substantially hand-shaped and ultimately forms the inner layer of a multilayer glove. The first and second layer-forming solutions may include elastomers curable to form a rubbery elastic surface. Preferably the layer-forming solutions include latex, but they may also include neoprene or vinyl.

The layer-forming solutions may comprise a release agent. "Release agent" is defined to mean a compound that is added to reduce the "stickiness" or "tackiness" of the layers. Thus the release agent may be added to reduce the tendency of the first layer to stick to the second layer. The layers may also be sprayed or coated with a release agent. Release agents may include soaps, silicone compounds, fluorinated polymers, or mixtures thereof.

Mold release agents commonly used to make vulcanized and unvulcanized elastomers less sticky may be used as release agents. For instance, mold release agents such as talcum and stearate compounds may be used as release agents.

Preferred release agents include organosiloxane (i.e. silicone) compounds. A silicone is generally defined as a compound that includes siloxane polymers which are based on a structure including alternate silicon and oxygen atoms, with organic radicals attached to the silicon.

A preferred release agent includes polydimethylsiloxane ("PDMS"). The layer-forming solutions and the gas-releasing solution may include about 0.001–3.0 weight percent of a release agent such as PDMS, preferably about 0.005–0.200 weight percent, more preferably about 0.01–0.05 weight percent, and more preferably still about 0.03 weight percent. PDMS sold under the trade name "Dow Corning 200 Fluid Food Grade 350CS" (Midland, Mich., U.S.A.) may be used as a release agent. In addition, "SM 2128 Silicone Emulsion" by General Electric Company (Waterford, N.Y., U.S.A.) may also be used as a release agent.

An excessive amount of PDMS (i.e., greater than about 5%) may cause larger and more numerous imperfections, thin areas, and pinholes to be formed in the layers. More-over, an excessive amount of release agent in the layers may increase the difficulty of sealing the layers to each other.

Other silicone compounds that may be used as release agents include compounds with PDMS structures. These PDMS structures may have disubstituted silicon atoms mixed with monosubstituted silicon atoms. The monosubstituted silicon atoms may have pendent groups such as methyl or phenyl. For instance, polyalkylene oxide modified diethylpolysiloxane may be used as a release agent.

Other release agents include: (1) stearates such as stearic acid (preferably about 0.1–1.0 weight percent, more preferably about 0.2–0.7 weight percent, and more preferably still about 0.25–0.50 weight percent) and zinc, aluminum, ammonium, barium, calcium and magnesium stearates, (2) fatty acids such as zinc oxide (preferably about 1.0–9.0 weight percent, more preferably about 2.0–8.0 weight percent, and more preferably still about 4.0–5.0 weight percent), fatty acid esters (preferably about 1.0–9.0 weight percent, more preferably about 2.0–8.0 weight percent, and more preferably still about 4.0–5.0 weight percent), sodium salts of fatty acid esters, saponified and highly saturated fatty acids, and hydrogenated fatty acids, (3) ethylenes such as ethylenebisoleamide (preferably about 0.1–2.75 weight percent, more preferably about 0.3–1.2 weight percent, and more preferably still about 0.3–0.5 weight percent), polyethylenes, ethylenebisstearamides, and ethylenebismonomerates, (4) glycols such as polyethylene glycols and polyalkylene glycols, and (5) other release agents such as ammonium salts of alkyl phosphate, polyethylenes, glycerine, vegetable oil soap, amorphous polypropylene, and straight chain alcohols.

In addition, release agents may include Mold Wiz AZN or Mold Wiz FFIH by Axel Plastic Research Laboratories, Inc. (Woodside, N.Y., U.S.A.) (preferably about 0.1–2.0 weight percent, more preferably about 0.1–1.0 weight percent, and more preferably still about 0.25–0.75).

After dipping the hand-shaped form into the first layer-forming solution, the first layer-forming material may be at least partially dried or cured. In this manner the first layer is more stable, and may be subsequently dipped without substantial wrinkling, oozing or dripping.

After forming the first layer, the first layer is dipped, preferably fingers first, into a gas-releasing solution that releases gas when heated. A "gas-releasing solution" is a solution that releases sufficient gas when heated to form a gas-filled layer separating the layers.

The gas-releasing solution may include a coagulant. A coagulant is defined to be a compound that coagulates a layer-forming solution so that the layer-forming solution forms a thicker layer than it would normally do otherwise. A coagulant is preferred because its presence may enhance the formation of the second layer on top of the damp or wet first layer. Without the coagulant the second layer tends to form irregularly. The type and concentration of coagulant may influence the thickness of layers formed. Other factors that may also influence the thickness of the layers formed include the immersion time of the form in the layer-forming solutions, and the viscosity of the layer-forming solutions.

The coagulant may comprise the following: acetic acid, calcium chloride, calcium nitrate, formic acid, zinc nitrate, or a mixture thereof. Preferably the coagulant is calcium nitrate. The gas-releasing solution may comprise about 10–50 weight percent of a coagulant such as calcium nitrate, preferably about 10–30 weight percent, more preferably about 15–25 weight percent, and more preferably still about 20 weight percent. The coagulant may also comprise a polysiloxane, which may also be mixed with the other coagulant compounds mentioned above.

The gas-releasing solution may comprise a blowing agent. A blowing agent is a compound that is stable at room temperature but which decomposes when heated to vulcanization temperatures to release gas. Vulcanization temperatures are typically about 140°–180° C. Vulcanization temperatures may vary depending on the vulcanization system—i.e., depending on the compounds vulcanized, the accelerators present, the vulcanization time, and other system-specific factors. Blowing agents are commonly used in the production of sponges.

The blowing agent may include sodium hydrogen carbonate (i.e., sodium bicarbonate). The gas-releasing solution may include about 5–25 weight percent of a blowing agent such as sodium hydrogen carbonate, preferably about 10–14 weight percent, and more preferably about 12 weight percent.

The blowing agent may include ammonium carbonate. The gas-releasing solution may include about 10–30 weight percent of a blowing agent such as ammonium carbonate, preferably about 12–18 weight percent, and more preferably about 15 weight percent.

Other blowing agents may be used. For instance, sodium bicarbonate in combination with a weak organic acid like tartaric, stearic- or oleic acid may be used. Sodium nitrite combined with ammonium chloride may be used. In addition, organic blowing agents such as (1) diazoamino compounds (e.g. diazoaminobenzene), (2) azonitrile, (3) azodicarbonamide, (4) hydrazine derivatives (e.g. benzenesulfohydrazide, benzene-1,3-disulfohydrazide, diphenyloxide-4,4'-disulfohydrazide, p-toluenesulfonic acid hydrazide), (5) n-nitroso compounds (e.g., n,n'-dinitrosopentamethylenetetramine and n,n'-dimethyl-n,n' -dinitrosophthalamide) (preferably about 20.0–80.0 weight percent, more preferably about 40.0–75.0 weight percent, and more preferably still about 65.0–70.0 weight percent), and (6) tartaric acid (preferably about 2.0–20.0 weight percent, more preferably about 5.0–15.0 weight percent, and more preferably still about 10.0–12.0 weight percent) may be used.

The toxicity and biocompatibility of the release agents, coagulants, and other compounds used in the solutions are also concerns when selecting such compounds for use for surgical gloves, condoms, etc.. In general it is preferred that such compounds be approved by the Food and Drug Administration.

The gas-releasing solution may include a release agent such as discussed above for the first layer-forming material. For example, the gas-releasing layer may include PDMS.

In a preferred embodiment only the gas-releasing solution includes a release agent. In a preferred embodiment the form is dipped into a first layer-forming solution to a first point. The form is then dipped into the gas-releasing solution to a second point that is short of the first layer-forming solution dip point. The form is then dipped into the second layer-forming solution to a third point that is beyond or past the second point. The third point may be before, at, or beyond the first point. In a preferred embodiment the first and second layers may be sealed together using the portions of these layers that have not contacted the release agent (i.e., the portion of these layers that was beyond or past the second point). Alternately, the first and second layers may be rolled together to form a beaded edge. The presence of the release agent in the portions of the first layer that were dipped into the gas-releasing solution may decrease the stickiness of the first and second layers to each other. The absence of the release agent from the portions of the first and second layer that are to be sealed tends to improve the seal between the layers.

The gas-releasing solution and the layer-forming solutions may additionally comprise an accelerator. An accelerator is preferably included in the layer-forming solutions. An accelerator is a compound that is added to shorten the amount of time and/or heat required to vulcanize the layer-forming solutions.

The gas-releasing solution is preferably allowed to at least partially dry. After the first layer is dipped into the gas-releasing solution, it is then dipped, preferably fingers first, into a second layer-forming solution to form a second layer. The second layer-forming solution may comprise the same components as described above for the first layer-forming solution. Preferably the second layer-forming solution comprises latex and PDMS, in the same preferred proportions as described above for the first layer-forming solution. Alternatively the layer-forming solutions may not include a release agent such as PDMS. Omitting the mold release agents from the layer-forming solutions may tend to reduce the number and size of imperfections (such as pinholes) formed in the layers.

The first or second layers are heated such that gas is released from the gas-releasing solution to form a gas-filled layer separating the first and second layers. Either or both of the first and second layers may be heated. Typically both the first and second layers are heated by placing these layers in an oven. When formed, the gas-filled layer substantially separates the first and second layers from each other. The release agent tends to facilitate separation of the layers. Without the release agent the layers tend to stick together, and the gas tends to form pockets instead of a gas-filled layer. Certain layer-forming solutions may be relatively "unsticky," and with these solutions no release agent may be required.

The first and second layers may be formed to comprise a wrist portion with an edge. The first layer may then be sealed to the second layer at the edge of the wrist portions of the first and second layers. The seal may form a cylindrical beaded edge. Alternately, the layers may be sealed together some distance from the edge.

In a preferred embodiment the antimicrobial solution replaces the gas in the gas-filled layer.

The first layer is preferably dipped to a first point into the gas-releasing solution which is typically about 1–3 centimeters ("cm") (preferably about 2–3 cm) from the full length mark. The top of the wrist portion of the first layer is considered the "full length mark." The length of the wrist portion may vary, depending on the length of wrist portion desired in the glove.

Preferably the gas-releasing solution is mixed and/or used at about 5–15° C. (preferably about 8–12° C., and more preferably about 10° C.), which is a temperature wherein the amount of calcium nitrate coagulant may be maximized in aqueous solutions. A preferred gas-releasing solution is saturated with a coagulant such as calcium nitrate. Preferably the first and second layers are heated to a temperature of about 140°–180° C. to form the gas-filled layer. Gloves made by the above-described method may be further washed to leach out remaining chemicals such as accelerators, gas-releasing solution, etc.

The gas-releasing solution and the layer-forming solutions may be in the form of a gel or a slurry. In a preferred embodiment the gas-releasing solution is a slurry. A slurry may be acceptable so long as the gas-releasing solution is substantially evenly distributed. A gas-releasing slurry solution may be beneficial since it may have more release agent, coagulant, or blowing agent present than is present in a saturated gas-releasing solution. Preferably the gas releasing solution is aqueous.

Another embodiment of the invention includes gloves made-according to the methods described above.

An alternate method of making a multilayer glove comprises the step of providing a first glove on a hand-shaped form instead of forming the first layer as described above. The glove is made of similar materials as described for first layer-forming solution. The glove acts as the first layer, and the steps described above for the first layer apply to the glove. Preferably the glove is initially green (i.e., unvulcanized).

An alternate embodiment of the invention is a multilayer condom. With the exception of the form shape, the condom is made with substantially similar materials and steps as outlined above for multilayer gloves. The first layer is formed by dipping a substantially penis-shaped form into a first layer-forming solution. The first layer is dipped into a gas-releasing solution that releases gas when heated. The first layer is then dipped into a second layer-forming solution to form a second layer. Heat is applied to the first or the second layer such that gas is released from the gas-releasing solution to form a gas-filled layer separating the first and second layers.

The layer-forming solutions, gas-releasing solutions, release agents, coagulants, blowing agents, and other materials for the condom are substantially the same as for the gloves mentioned above. In addition, a multilayer condom may be made by providing a first (preferably green) condom on a penis-shaped form as an alternate way to form the first layer.

Another embodiment of the invention includes condoms made according to the methods outlined above.

Another embodiment of the invention includes finger cots, and methods of making finger cots. The finger cots are made in a substantially similar way as the condoms of the invention are made. With the exception of the form, the materials, steps, agents, solutions, etc. outlined above for condoms will apply to finger cots. A finger cot is made with a substantially finger-shaped form.

Figure 4:
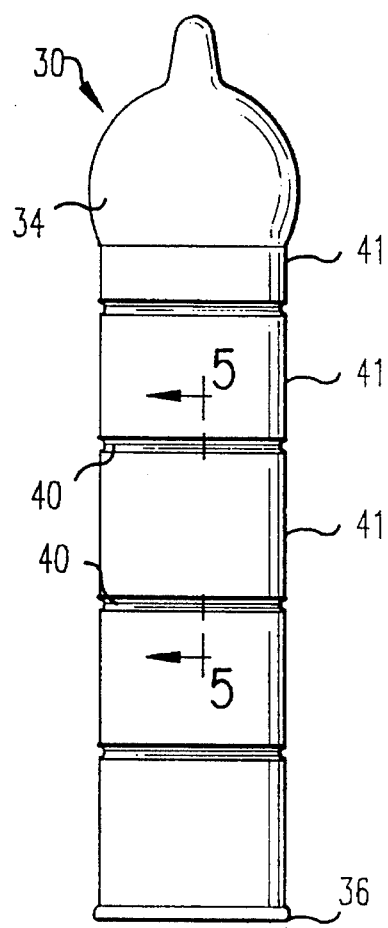
FIG. 4 is a side view of a condom prepared according to the present invention.
Figure 5:
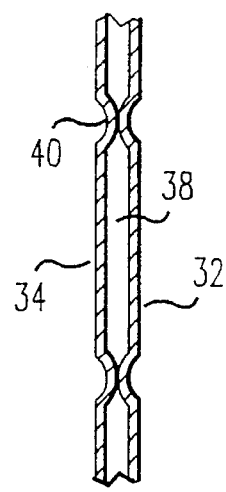
FIG. 5 is a fragmentary, sectional view of the condom taken at the position shown in FIG. 4.

Referring now to FIGS. 4 and 5, a preferred embodiment of a condom 30 as provided by the present invention is illustrated. The condom 30 includes an inner layer 32, and outer layer 34, and an impermeable seal 36 between the inner and outer layers at the rim of the condom. A layer of spermicidal solution 38 (thickness as described above), such as nonoxynol-9, is disposed between the inner layer 32 and outer layer 34. Nonoxynol-9 is preferred, as it is both spermicidal to reduce the risk of pregnancy and virucidal for protection against harmful viruses such as HIV. The layers may be made of materials conventionally used for making condoms.

In order to reduce the likelihood of the layers 32 and 34 from slipping on each other during use, the layers may be sealed together at a plurality of points. In the embodiment shown, the condom 30 is provided with a plurality of circular heat stamped lines 40, dividing the condom into distinct compartments 41 along its length. In this arrangement, the protective fluid 38 may be prevented from squeezing to the base of the condom during use, as each heat stamped line 40 will restrict fluid flow between adjacent compartments 41. The heat stamped lines may be formed by heating and pressing the inner and outer layers together at the desired places for a sufficient length of time for a seal to form.

Figure 6:
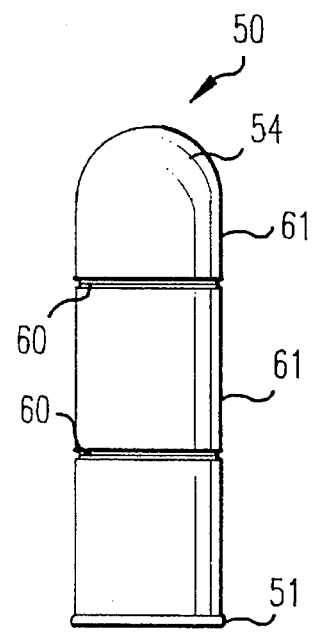
FIG. 6 is a side view of a finger cot prepared according to the present invention.

Referring now to FIG. 6, a preferred embodiment of a finger cot 50 is illustrated. Similar to the surgical glove described above, the finger cot 50 includes an inner layer, an outer layer 54, an impermeable seal 56 between the inner and outer layers, and a layer of antimicrobial solution (thickness as described above) disposed between the layers. (It should be noted that a sectional view of the sidewall of the finger cot would look substantially similar to FIG. 5). The preferred materials for use as the layers and antimicrobial solution discussed above in connection with surgical gloves also apply to the finger cot 50.

Since finger cots are conventionally used for procedures such as rectal or vaginal examinations, it is desirable to seal the inner layer 52 and outer layer 54 together at a plurality of points to reduce the likelihood of disassembly during use. In the embodiment shown, the finger cot 50 is heat stamped with several circular lines 60, compartmentalizing the finger cot into isolated sections 61. As with the condom described above, this embodiment prevents the antimicrobial solution from accumulating at the base of the finger cot during use.

The following experiment was designed to demonstrate the capillary coupling force exerted by a liquid layer between two latex surfaces as a function of the thickness of the liquid layer. This was accomplished by measuring the average failure load ("AFL") in g/cm$^2$, between two glass carriers coated with vulcanized latex, having a fluid layer of varying thickness therebetween.

Figure 7:
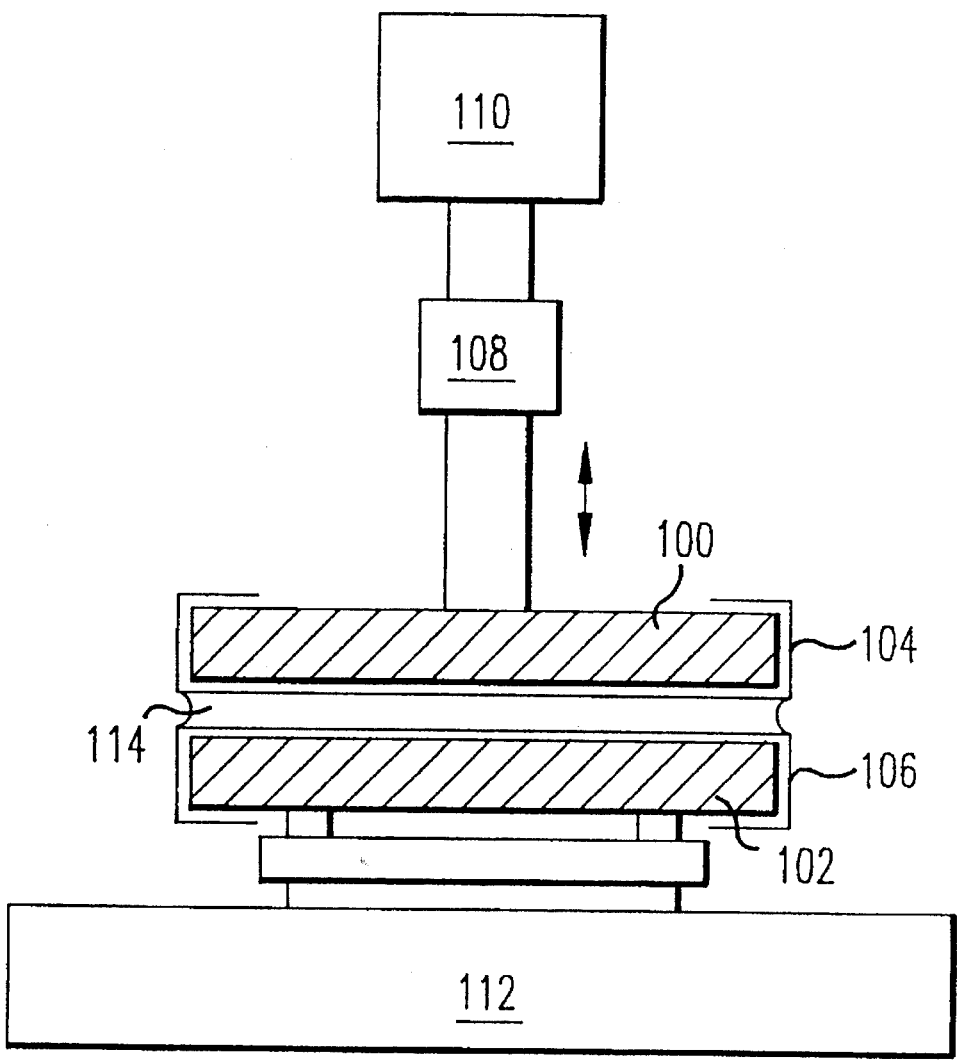
FIG. 7 is a schematic diagram of the apparatus used in the example below.

FIG. 7 illustrates the apparatus used in the experiment. Two pieces of latex material 104 and 106 were glued onto the surface of two glass carriers 100 and 102, respectively. The pieces of latex were obtained from Travenol Triflex Sterile Latex Surgeons Gloves, size 8.5, in which powder had been removed by washing three times in 2 liters aqua bidet. The latex layers 104 and 106 were each 0.18 mm thick, while each glass carrier 100 and 102 was 6 mm thick.

Glass carrier 100 was mechanically connected to a micrometer 108 with 0.01 mm resolution. The glass carriers were kept in substantially parallel alignment during movement. The micrometer 108 was driven by a stepping motor 110 at a rate of 1 mm/min.

Glass carrier 102 was preweighted with 300 g and connected to a rapidly indicating electronic balance 112. The contact area between the two carriers 100 and 102 was 2 in$^2$ (~25.81 cm$^2$).

Volumes ranging from 10 µl to 500 µl of colored bactericidal fluid 114, were pipetted onto the surface of carrier 102, and carrier 100 was lowered until the liquid 114 covered the entire contact area.

Carrier 100 was then lifted at a constant time rate by the stepper motor 110 via the micrometer 108. The maximum decrease in weight, indicated by the electronic balance 112, was reached shortly before rupture of the liquid layer 114 and noted.

Each experiment for a specific liquid volume was repeated seven times.

Figure 8:
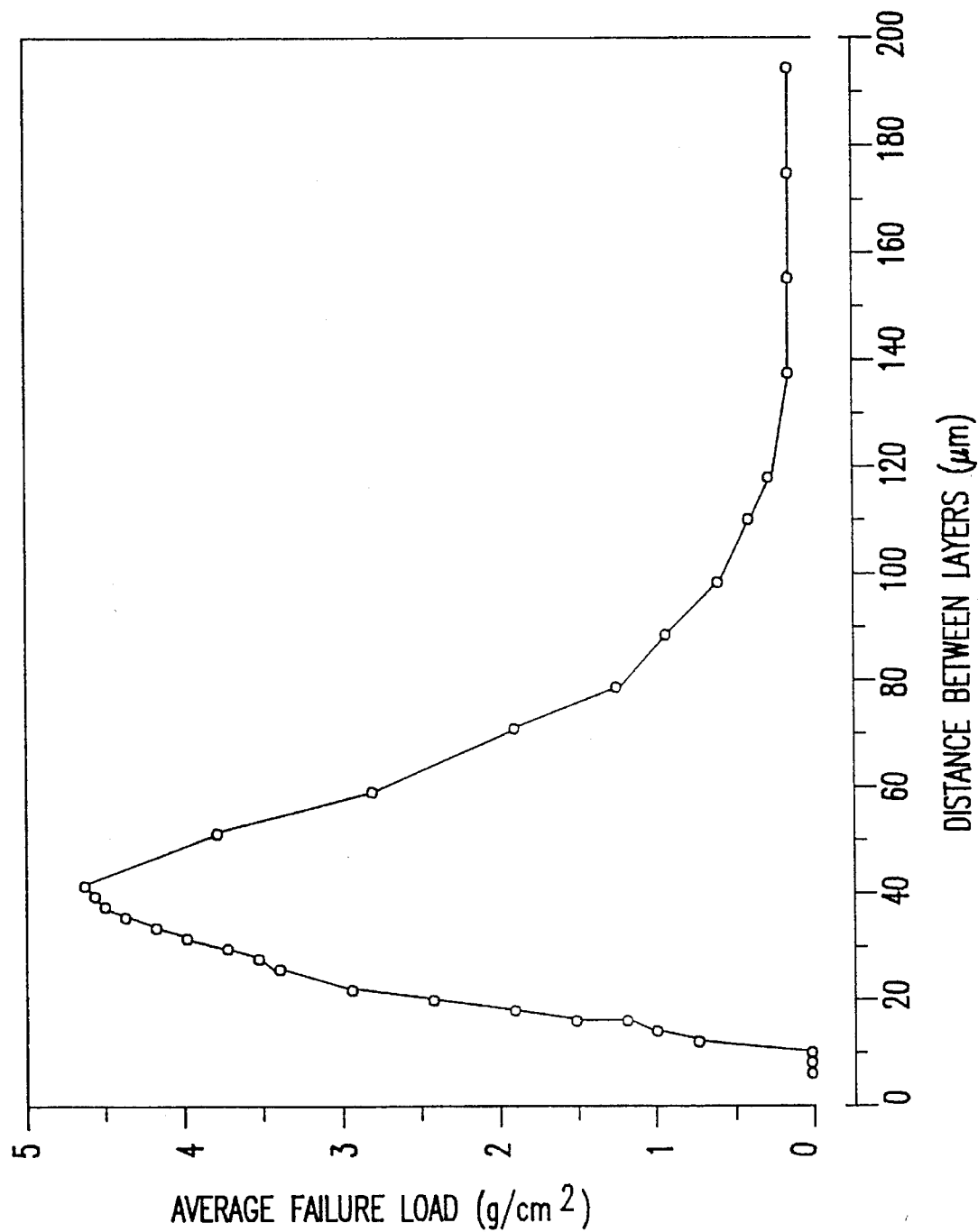
FIG. 8 is a plot of the experimental results of the example below.

The results of the experiment are shown in Table 1 and FIG. 8. The maximum AFL was reached at a liquid volume of around 100 µl (~0.039 mm fluid layer thickness). The AFL approached zero at volumes above 300 µl (~0.116 mm thick).

For comparison, the last column of Table 1 gives the required liquid volume, corresponding to the given liquid layer thickness, for a glove size 8.5 (surface area ~650 cm$^2$). Thus, for example, to obtain a fluid layer thickness of 0.039 mm between two size 8.5 gloves would require a fluid volume of about 2.518 ml.

TABLE 1

| LIQUID VOLUME (µl) | DISTANCE BETWEEN CARRIERS (LIQUID LAYER THICKNESS) (mm) | AVERAGE FAILURE LOAD (g/cm$^2$) | EQUIVALENT LIQUID VOLUME FOR GLOVE (ml/650 cm$^2$) |
|---|---|---|---|
| 10 | 0.004 | 0.000 | 0.252 |
| 15 | 0.006 | 0.000 | 0.378 |
| 20 | 0.008 | 0.000 | 0.504 |
| 25 | 0.010 | 0.697 | 0.630 |
| 30 | 0.012 | 0.969 | 0.756 |
| 35 | 0.014 | 1.124 | 0.881 |
| 40 | 0.015 | 1.434 | 1.007 |
| 45 | 0.017 | 1.860 | 1.133 |
| 50 | 0.019 | 2.402 | 1.259 |
| 55 | 0.021 | 2.867 | 1.385 |
| 60 | 0.023 | 3.371 | 1.511 |
| 65 | 0.025 | 3.487 | 1.637 |
| 70 | 0.027 | 3.681 | 1.763 |
| 75 | 0.029 | 3.952 | 1.889 |
| 80 | 0.031 | 4.184 | 2.015 |
| 85 | 0.033 | 4.339 | 2.141 |
| 90 | 0.035 | 4.456 | 2.267 |
| 95 | 0.037 | 4.494 | 2.392 |
| 100 | 0.039 | 4.611 | 2.518 |
| 125 | 0.048 | 3.719 | 3.148 |
| 150 | 0.058 | 2.751 | 3.778 |
| 175 | 0.068 | 1.860 | 4.407 |
| 200 | 0.077 | 1.162 | 5.037 |
| 225 | 0.087 | 0.814 | 5.666 |
| 250 | 0.097 | 0.504 | 6.296 |
| 275 | 0.107 | 0.310 | 6.926 |
| 300 | 0.116 | 0.116 | 7.555 |
| 350 | 0.136 | 0.000 | 8.814 |

TABLE 1-continued

| LIQUID VOLUME (μl) | DISTANCE BETWEEN CARRIERS (LIQUID LAYER THICKNESS) (mm) | AVERAGE FAILURE LOAD (g/cm$^2$) | EQUIVALENT LIQUID VOLUME FOR GLOVE (ml/650 cm$^2$) |
|---|---|---|---|
| 400 | 0.155 | 0.000 | 10.074 |
| 450 | 0.174 | 0.000 | 11.333 |
| 500 | 0.194 | 0.000 | 12.592 |

The instant invention has been disclosed in connection with specific embodiments. However, it will be apparent to those skilled in the art that variations from the illustrated embodiments may be undertaken without departing the spirit and scope of the invention. For example, in connection with jobs where it is required that gloves be discarded after a certain amount of use, e.g. four hours, an absorption indicating substance might be placed between the glove layers to, e.g., change colors upon a certain degree of absorption.

I claim:

1. A method for making a multilayer glove, comprising the steps of:

dipping a substantially hand-shaped form into a first layer-forming solution to form a first layer on the hand-shaped form;

dipping the first layer into a gas-releasing solution that releases gas when heated to deposit a single substantially continuous layer of the gas-releasing solution on the first layer;

dipping the first layer into a second layer-forming solution to form a second layer, such that the gas-releasing solution is disposed between the first and second layers; and heating the first or second layer such that gas is released from the gas-releasing solution to form a single substantially continuous gas-filled layer separating the first and second layers.

2. A method for making a multilayer glove, comprising the steps of:

dipping a substantially hand-shaped form into a first layer-forming solution to a first point on the hand-shaped form to form a first layer on the hand-shaped form;

dipping the first layer to a second point on the hand-shaped form short of the first point into a gas-releasing solution that releases gas when heated to deposit a single substantially continuous layer of the gas-releasing solution on the first layer;

dipping the first layer to a third point on the hand-shaped form located past the second point into a second layer-forming solution to form a second layer, such that the gas-releasing solution is disposed between the first and second layers; and heating the first or second layer such that gas is released from the gas-releasing solution to form a single substantially continuous gas-filled layer separating the first and second layers.

3. The method of claim 1, further comprising the step of replacing gas in the gas-filled layer with an antimicrobial solution.

4. The method of claim 2, further comprising the step of replacing gas in the gas-filled layer with an antimicrobial solution.

5. The method of claim 1 wherein the first and second layers are both formed to comprise a wrist portion with an edge, and further comprising the step of sealing the first layer to the second layer at the edge of the wrist portions.

6. The method of claim 5 wherein an antimicrobial solution is sealed between the first layer and the second layer.

7. The method of claim 2 wherein the first and second layers are both formed to comprise a wrist portion with an edge, and further comprising the step of sealing the first layer to the second layer at the edge of the wrist portions.

8. The method of claim 7 wherein an antimicrobial solution is sealed between the first layer and the second layer.

9. The method of claim 1 wherein the first layer-forming solution comprises a release agent.

10. The method of claim 1 wherein the second layer-forming solution comprises a release agent.

11. The method of claim 1 wherein the gas-releasing solution comprises a release agent.

12. The method of claim 1 wherein the first layer-forming solution comprises a silicone compound.

13. The method of claim 1 wherein the second layer-forming solution comprises a silicone compound.

14. The method of claim 1 wherein the gas-releasing solution comprises a silicone compound.

15. The method of claim 1 wherein the first layer-forming solution comprises polydimethylsiloxane.

16. The method of claim 1 wherein the second layer-forming solution comprises polydimethylsiloxane.

17. The method of claim 1 wherein the gas-releasing solution comprises polydimethylsiloxane.

18. The method of claim 1 wherein the first layer-forming solution comprises about 0.001–3.0 weight percent polydimethylsiloxane.

19. The method of claim 1 wherein the first layer-forming solution comprises about 0.005–0.2 weight percent polydimethylsiloxane.

20. The method of claim 1 wherein the first layer-forming solution comprises about 0.01–0.05 weight percent polydimethylsiloxane.

21. The method of claim 1 wherein the second layer-forming solution comprises about 0.001–3.0 weight percent polydimethylsiloxane.

22. The method of claim 1 wherein the second layer-forming solution comprises about 0.005–0.2 weight percent polydimethylsiloxane.

23. The method of claim 1 wherein the second layer-forming solution comprises about 0.01–0.05 weight percent polydimethylsiloxane.

24. The method of claim 1 wherein the gas-releasing solution comprises about 0.001–3.0 weight percent polydimethylsiloxane.

25. The method of claim 1 wherein the gas-releasing solution comprises about 0.005–0.2 weight percent polydimethylsiloxane.

26. The method of claim 1 wherein the gas-releasing solution comprises about 0.01–0.05 weight percent polydimethylsiloxane.

27. The method of claim 1 wherein the first layer-forming solution comprises latex.

28. The method of claim 1 wherein the second layer-forming solution comprises latex.

29. The method of claim 1 wherein the gas-releasing solution comprises a coagulant.

30. The method of claim 29 wherein the coagulant is acetic acid, calcium chloride, calcium nitrate, a polysiloxane, formic acid, or zinc nitrate.

31. The method of claim 1 wherein the gas-releasing solution comprises calcium nitrate.

32. The method of claim 1 wherein the gas-releasing solution comprises about 10–50 weight percent calcium nitrate.

33. The method of claim 1 wherein the gas-releasing solution comprises about 10–30 weight percent calcium nitrate.

34. The method of claim 1 wherein the gas-releasing solution comprises about 15–25 weight percent calcium nitrate.

35. The method of claim 1 wherein the gas-releasing solution comprises a blowing agent.

36. The method of claim 1 wherein the gas-releasing solution comprises sodium hydrogen carbonate.

37. The method of claim 1 wherein the gas-releasing solution comprises about 5–25 weight percent sodium hydrogen carbonate.

38. The method of claim 1 wherein the gas-releasing solution comprises about 10–14 weight percent sodium hydrogen carbonate.

39. The method of claim 1 wherein the gas-releasing solution comprises ammonium carbonate.

40. The method of claim 1 wherein the gas-releasing solution comprises about 10–30 weight percent ammonium carbonate.

41. The method of claim 1 wherein the gas-releasing solution comprises about 12–18 weight percent ammonium carbonate.

42. The method of claim 1 wherein the gas-releasing solution is about 8°–12° C.

43. The method of claim 1 wherein the gas-releasing solution is about 5–15° C.

44. The method of claim 1, further comprising the step of at least partially drying the first layer before dipping into the gas-releasing solution.

45. The method of claim 1, further comprising the step of at least partially drying the gas-releasing solution before dipping into the second layer-forming solution.

46. The method of claim 7 wherein the first point is about 1–3 centimeters from the edge of the wrist portion.

47. A method of making a multilayer glove, comprising the steps of:

providing a first glove on a substantially hand-shaped form;

dipping the first glove into a gas-releasing solution that releases gas when heated to deposit a single substantially continuous layer of the gas-releasing solution on the first glove;

dipping the first glove into a layer-forming solution to form an outer layer, such that the gas-releasing solution is disposed between the first glove and the outer layer; and heating the first glove or the outer layer such that gas is released from the gas-releasing solution to form a single substantially continuous gas-filled layer separating the first glove and the outer layer.

48. The method of claim 47, further comprising the step of replacing the gas in the gas-filled layer with an antimicrobial solution.

* * * * *